(12) United States Patent
Hwang

(10) Patent No.: US 9,521,202 B2
(45) Date of Patent: Dec. 13, 2016

(54) METHOD FOR MATCHING MULTIPLE DEVICES, AND DEVICE AND SERVER SYSTEM FOR ENABLING MATCHING

(71) Applicant: FuturePlay Inc., Seoul (KR)

(72) Inventor: Sung Jae Hwang, Seoul (KR)

(73) Assignee: FuturePlay Inc. (KR)

( * ) Notice: Subject to any disclaimer, the term of this patent is extended or adjusted under 35 U.S.C. 154(b) by 0 days.

(21) Appl. No.: 14/807,583

(22) Filed: Jul. 23, 2015

(65) Prior Publication Data

US 2015/0334189 A1 Nov. 19, 2015

Related U.S. Application Data

(63) Continuation-in-part of application No. PCT/KR2014/004427, filed on May 16, 2014.

(30) Foreign Application Priority Data

May 16, 2013 (KR) ........................ 10-2013-0055581

(51) Int. Cl.
| | | |
|---|---|---|
| *H04L 29/08* | (2006.01) | |
| *G06F 19/00* | (2011.01) | |
| *G06F 3/01* | (2006.01) | |
| *G06F 17/30* | (2006.01) | |
| *H04L 12/28* | (2006.01) | |
| *H04W 4/00* | (2009.01) | |
| *H04W 4/20* | (2009.01) | |

(52) U.S. Cl.
CPC ............ *H04L 67/125* (2013.01); *G06F 3/017* (2013.01); *G06F 17/30864* (2013.01); *G06F 19/3406* (2013.01); *H04L 12/2807* (2013.01); *H04W 4/005* (2013.01); *H04W 4/206* (2013.01)

(58) Field of Classification Search
CPC G06F 19/3406; G06F 3/017; G06F 17/30864; H04L 12/2807; H04L 67/125
See application file for complete search history.

(56) References Cited

U.S. PATENT DOCUMENTS

| | | | |
|---|---|---|---|
| 2012/0075439 A1* | 3/2012 | Gong | H04N 5/247 348/61 |
| 2012/0263154 A1* | 10/2012 | Blanchflower | G06F 17/30247 370/338 |
| 2013/0002417 A1* | 1/2013 | Akiyama | B60W 40/08 340/439 |

FOREIGN PATENT DOCUMENTS

| | | |
|---|---|---|
| KR | 10-2011-0088936 A | 8/2011 |
| KR | 10-2011-0096005 A | 8/2011 |
| KR | 10-2012-0071202 A | 7/2012 |
| KR | 10-2013-0043935 A | 5/2013 |

* cited by examiner

*Primary Examiner* — Michael C Lai
(74) *Attorney, Agent, or Firm* — Dinsmore & Shohl LLP; Yongsok Choi

(57) ABSTRACT

The present invention relates to a method for matching multiple devices, and a device and a server system for enabling the matching thereof. According to one aspect of the invention, provided is a matching method comprising the steps of: determining, from a perspective of a first device, characteristic information on a biological state of a user, and independently determining, from a perspective of a second device, characteristic information associated with or generated according to the biological state of the user; and matching the first device and the second device on the basis of the characteristic information determined from the perspective of the first device and the characteristic information determined from the perspective of the second device.

17 Claims, 9 Drawing Sheets

METHOD FOR MATCHING MULTIPLE DEVICES, AND DEVICE AND SERVER SYSTEM FOR ENABLING MATCHING

PRIORITY CLAIM

This application is a continuation-in-part application of Patent Cooperation Treaty (PCT) international application Serial No. PCT/KR2014/004427, filed on May 16, 2014 and which designates the United States, which claims the benefit of the filing date of Korean Patent Application Serial No. 10-2013-0055581, filed on May 16, 2013. The entirety of both PCT international application Serial No. PCT/KR2014/004427 and Korean Patent Application Serial No. 10-2013-0055581 are incorporated herein by reference.

FIELD OF THE INVENTION

The present invention relates to a method for matching multiple devices, and a device and a server system for enabling the matching thereof.

BACKGROUND

Recently, mobile smart devices having various communication and sensing capabilities and powerful computing capabilities, such as smart phones and smart pads, are being widely used. Among such mobile smart devices, there are relatively small-sized ones that may be worn and carried on a body of a user (e.g., a smart glass, a smart watch, a smart band, a smart device in the form of a ring or a brooch, a smart device directly attached to or embedded in a body or a garment, etc.)

In this situation, a user may desire to perform a task using two or more (different kinds of) smart devices of the user, or may desire a task to be performed in which smart devices of the user and another user are required to be involved together. However, this (latent) intention of the user could not have been properly supported in prior art.

SUMMARY OF THE INVENTION

One object of the present invention is to fully solve the above problem in prior art.

Another object of the invention is to provide a novel technique for matching multiple devices.

Yet another object of the invention is to allow the matching of multiple devices to enable the realization of applied techniques.

According to one aspect of the invention to achieve the objects as described above, there is provided a matching method comprising the steps of: determining, from a perspective of a first device, characteristic information on a biological state of a user, and independently determining, from a perspective of a second device, characteristic information associated with or generated according to the biological state of the user; and matching the first device and the second device on the basis of the characteristic information determined from the perspective of the first device and the characteristic information determined from the perspective of the second device.

In addition, there are further provided other methods, devices, and matching systems to implement the invention.

According to the invention, a novel technique for matching multiple devices is provided.

According to the invention, the matching of multiple devices enables the realization of applied techniques.

DETAILED DESCRIPTION OF THE PREFERRED EMBODIMENTS

Figure 1:
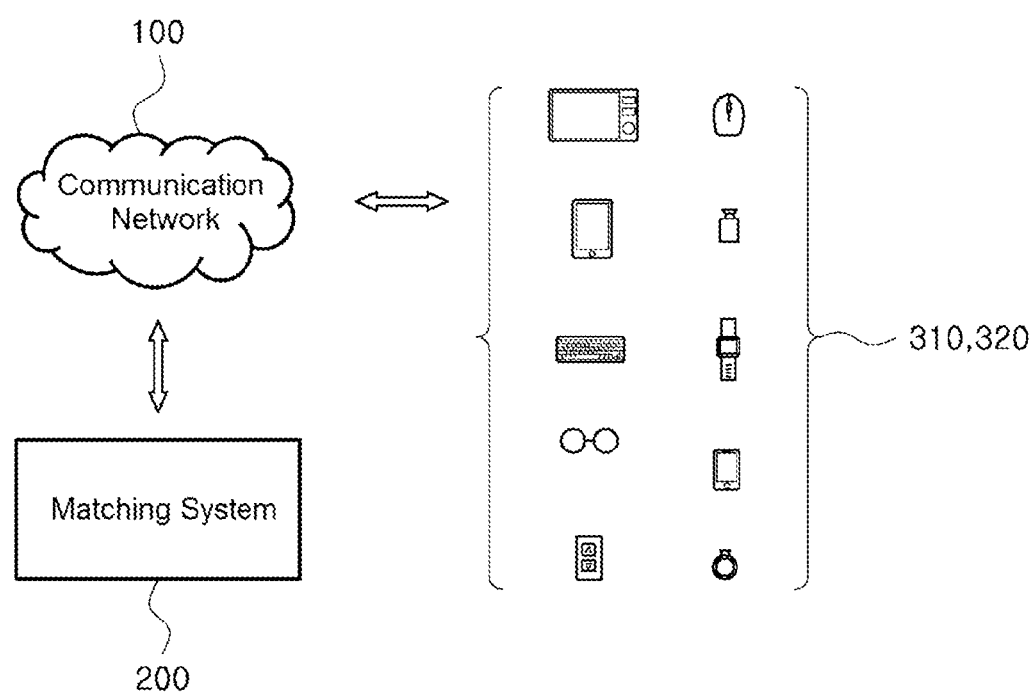
FIG. 1 is a schematic diagram showing the configuration of an entire system for matching multiple devices according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the locations or arrangements of individual elements within each of the embodiments may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Configuration of an Entire System

FIG. 1 is a schematic diagram showing the configuration of an entire system for matching multiple devices according to one embodiment of the invention.

As shown in FIG. 1, the entire system according to one embodiment of the invention may comprise a communication network 100, a matching system 200, and multiple devices 310, 320.

First, the communication network 100 according to one embodiment of the invention may be implemented regardless of communication modality such as wired and wireless communications, and may be constructed from a variety of communication networks such as local area networks (LANs), metropolitan area networks (MANs), and wide area networks (WANs). Preferably, the communication network 100 described herein may be the Internet or the World Wide Web (WWW). However, the communication network 100 is not necessarily limited thereto, and may at least partially include known wired/wireless data communication networks, known telephone networks, or known wired/wireless television communication networks.

Next, the matching system 200 according to one embodiment of the invention may be digital equipment having a memory means and a microprocessor for computing capabilities. The matching system 200 may be a server system.

Figure 3:
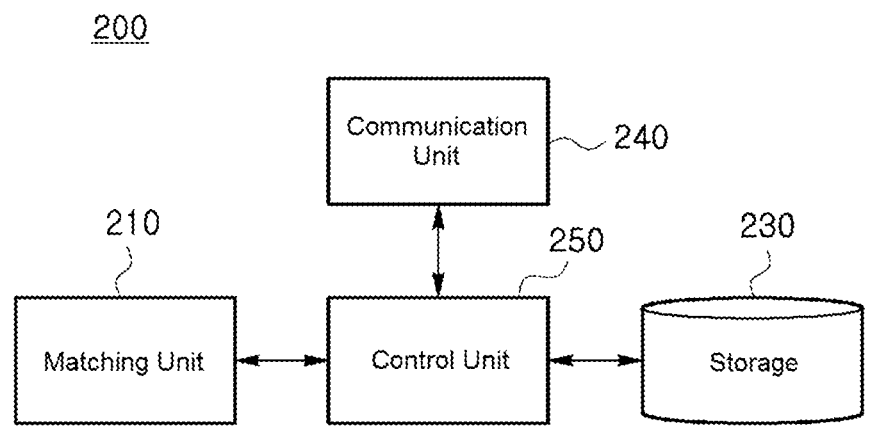
FIG. 3 is a schematic diagram showing the configuration of a matching system according to one embodiment of the invention.

FIG. 3 is a schematic diagram showing the configuration of the matching system according to one embodiment of the invention. As shown in FIG. 3, the matching system 200 may comprise a matching unit 210, a storage 230, a communication unit 240, and a control unit 250. According to one embodiment of the invention, at least some of the matching unit 210, the storage 230, the communication unit 240, and the control unit 250 may be program modules to communicate with at least one of the multiple devices 310, 320. The program modules may be included in the matching system 200 in the form of operating systems, application program modules or other program modules, while they may be physically stored on a variety of commonly known storage devices. Further, the program modules may also be stored in a remote storage device that may communicate with the matching system 200. Meanwhile, such program modules may include, but not limited to, routines, subroutines, programs, objects, components, data structures and the like for performing specific tasks or executing specific abstract data types as will be described below in accordance with the invention. Particularly, the matching system 200 may function to mediate so that via the communication network 100, one of the devices 310, 320 may transmit information or a control command to the other, or the one may receive information or a control command from the other.

To this end, as will be described in detail below, the matching system 200 may receive one type of temporary or non-temporary characteristic information on a specific user (possibly a user of a first device 310) from the first device 310 and receive the same or another type of temporary or non-temporary characteristic information on the specific user from a second device 320, and then may compare or collate the pieces of the information to recognize that the first device 310 and the second device 320 have an association (e.g., indicating that they belong to the same user, they function for the sake of the same user, they are located substantially close to each other, or one of them is competent to authenticate or permit the other). (Hereinafter, such recognition itself, or formation of a connection between the devices 310, 320 according to the recognition, is mainly referred to as "matching" for convenience.) The matching may be permanent, but may preferably be maintained only for a predetermined time period and then released.

The matching may be performed by the matching unit 210 included in the matching system 200. The matching unit 210 may reside in the matching system 200 in the form of a program module as described above.

Further, the matching system 200 may further function to store information provided from at least one of the devices 310, 320 and allow the information to be used by at least one of the devices 310, 230 or by another third device (not shown). The storing may be performed by the storage 230 included in the matching system 200. The storage 230 encompasses a computer-readable recording medium, and may refer not only to a database in a narrow sense but also to a database in a broad sense including file system-based data records and the like.

Meanwhile, the communication unit 240 in the matching system 200 may function to enable data transmission/receipt to/from the matching unit 210 and the storage 230.

Further, the control unit 250 in the matching system 200 may function to control data flow among the matching unit 210, the storage 230, and the communication unit 240. That is, the control unit 250 according to the invention may control data flow into/out of the matching system 200 or data flow among the respective components of the matching system 200, such that the matching unit 210, the storage 230, and the communication unit 240 may carry out their particular functions, respectively.

The function of the matching system 200 will be discussed in more detail below. Meanwhile, although the matching system 200 has been described as above, the above description is illustrative and it is apparent to those skilled in the art that at least some of the functions or components required for the matching system 200 may be implemented or included in another third device, and even in at least one of the devices 310, 320 to be matched, as necessary.

Figure 4A:
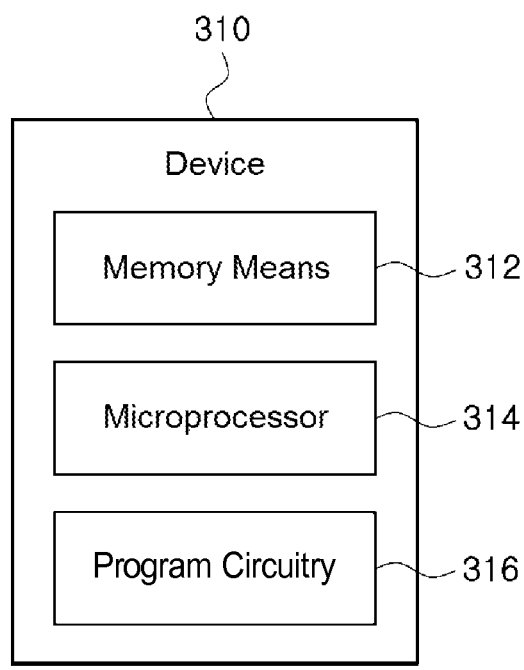
FIGS. 4A and 4B are schematic diagrams showing the configurations of devices according to one embodiment of the invention.
Figure 4B:
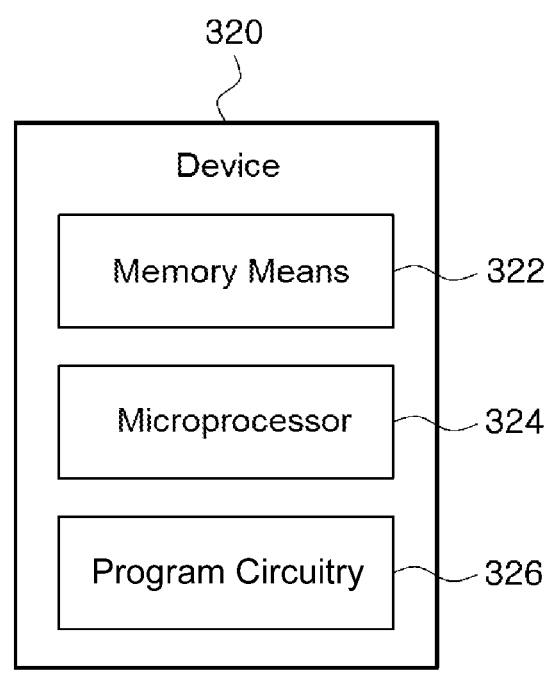

Lastly, the multiple devices 310, 320 according to one embodiment of the invention are digital equipment that may function to connect to and then communicate with the matching system 200, a counterpart of the multiple devices 310, 320 (which may preferably be separated or externalized from each other), or another third device, and any type of digital equipment having memory means 312, 322 and microprocessors 314, 324 for computing capabilities may be adopted as the devices 310, 320 according to the invention. The devices 310, 320 may be so-called smart devices such as a smart phone, a smart pad, a smart glass, a smart watch, a smart band, and a smart ring, or may be somewhat traditional devices such as a desktop computer, a notebook computer, a workstation, a personal digital assistant (PDA), a web pad, a mobile phone, buttons, a mouse, a keyboard, and an electronic pen. Meanwhile, the devices 310, 320 may further include technical means (not shown) and program circuitry 316, 326 to be described below. In connection with the schematic configurations of the devices 310, 320 according to one embodiment of the invention, further reference may be made to FIGS. 4A and 4B, respectively.

Particularly, the devices 310, 320 may include at least one technical means for calculating a physical or chemical value regarding a biological state of a specific user. Examples of the technical means may include commonly known components such as a brainwave sensor, a respiration sensor, a pulsation sensor, an electrocardiogram sensor, an electromyogram sensor (possibly a multi-channel electromyogram sensor for obtaining comprehensive information on muscular movement and the like), a camera, a touch sensor, a pressure sensor, buttons, keys, a graphical object operable by the user, and the like.

Further, the devices 310, 320 may further include an application program for processing the above value to transmit information or a control command to another device (310, 320, or the like), to receive information or a control command from another device (310, 320, or the like), or to generate the information or control command. The application may reside in the corresponding devices 310, 320 in the form of program modules. The program circuitry 316, 326 operates or executes the program modules in communication with the microprocessors 314, 324. The nature of the program modules may be generally similar to that of the aforementioned matching unit 210 of the matching system 200.

Meanwhile, when the matching is made between the devices 310, 320, the application may control the devices 310, 320 to make some response so that a user may notice the matching. For example, the devices 310, 320 may provide the user with a visual, aural, or tactual response. The response may be, for example, displaying of a matching report message, emitting of a clear matching report sound, a matching report vibration that may be sensed in a hand, or the like.

Meanwhile, at least a part of the application may be replaced with a hardware or firmware device that may perform a substantially equal or equivalent function, as necessary.

The function of the application will be discussed in detail below.

Matching Methods

Hereinafter, specific examples of methods for matching the multiple devices 310, 320 according to various embodiments of the invention will be discussed in detail.

First embodiment

According to the embodiments, the first device 310 and the second device 320 may be matched on the basis of information on a biological state of a specific user, which is identified by the first device 310, and information associated with or generated according to the above state, which is identified by the second device 320. Preferably, the first device 310 may be a device such as a smart phone, a smart glass and a smart watch, which is frequently carried by the user, and in many cases, is considered to be suitable to store and process important information of the user.

First, it is assumed that the user has shown a biological state to the first device 310. In this case, the first device 310 may calculate a physical or chemical value regarding at least one of brainwave, respiration, pulsation, electrocardiogram, electromyogram, nictitation, complexion, blood vessel color, skin color, muscular movement, and muscular separation of the user, by means of at least one of a brainwave sensor, a respiration sensor, a pulsation sensor, an electrocardiogram sensor, an electromyogram sensor, a camera (capable of observing nictitation, complexion, blood vessel color, skin color, muscular movement, muscular separation, etc.), and an optical sensor (capable of sensing blood vessel color, skin color, etc.), which may be embedded therein or associated therewith. Here, the pattern over time of the above biological information of the user may be highly singular information that is actually indicative of the user. Meanwhile, the brainwave, electromyogram, muscular movement, muscular separation, and the like may represent a gesture of the user to be described below.

Next, on the basis of the calculated value, an application (not shown) of the first device 310 may determine a pattern regarding the biological state of the user, and the determined pattern may be captured within a time window of a length adjustable as necessary. Further, the pattern may be represented by a wave over a specific period of time, or by appropriately normalizing, scaling, or quantizing such a wave.

The application of the first device 310 may determine the pattern itself determined and represented as above, or property information obtained by analyzing the determined pattern, as highly characteristic information on the first device 310. (This characteristic information may be referred to as "characteristic information from a perspective of the first device.") The characteristic information on the first device 310 may be provided to the matching system 200. Further, the characteristic information may be provided from the first device 310 to the second device 320, by means of the matching system 200 or not.

Hereinafter, it will be discussed how the matching is achieved between the first device 310 and the second device 320 on the basis of the characteristic information on the first device 310.

(1) The case in which the second device 320 observes nictitation, complexion, blood vessel color, skin color, muscular movement, muscular separation, and the like of a user of the first device 310

It is assumed that the second device 320 includes or communicates with a camera or an optical sensor to observe or photograph at least one of nictitation, complexion, blood vessel color, skin color, muscular movement, and muscular separation of a user of the first device 310. An application (not shown) of the second device 320 may determine a specific pattern from a series of images photographed regarding at least one of the nictitation, complexion, blood vessel color, skin color, muscular movement, and muscular separation of the user of the first device 310, or from data obtained by optically sensing the blood vessel color or skin color of the user of the first device 310. In this case, the time window employed for the pattern determination may be substantially equal to, or a multiple of, that employed in determining the characteristic information from the perspective of the first device 310. Accordingly, the second device 320 may independently determine characteristic information on at least one of the nictitation, complexion, blood vessel color, skin color, muscular movement, and muscular separation of the user of the first device 310 (i.e., the pattern itself, or property information obtained by analyzing the pattern). (This characteristic information, and similar information to be described below, may be referred to as "characteristic information from a perspective of the second device.") The determined information may also be provided to the matching system 200, or may be provided to the first device 310, if necessary.

The matching system 200, the first device 310, or the second device 320 may match the first device 310 and the second device 320 on the basis of a combination of the characteristic information respectively determined regarding the biological state of the user of the first device 310, and may accordingly notify the matching to at least one of the first device 310 and the second device 320. Here, it is important that the combination may be regarding not only the same type but also different types of biological state pattern information. That is, if two biological states, although of different types, are closely associated with each other, the patterns of the two biological states may be very similar even though the units of the values thereof, for example, may be different. For example, the pattern of the values sensed by an electromyogram sensor of the first device 310 regarding one of the neck, wrist, ankle, finger, and the like of the user may be very similar to that obtained from a series of images in which muscular movement of the corresponding body part is photographed by a camera of the second device 320. Further, for example, the pattern of the values sensed by a pulsation sensor of the first device 310 regarding the user may be very similar to that obtained from a series of images in which color of the face of the user is photographed by a camera of the second device 320.

At least one of the first device 310 and the second device 320 may perform various processes on the basis of the matching. For example, it is enabled that information (e.g. a computer file) is transmitted or received between the devices 310, 320, or that one of the devices 310, 320 or the user thereof performs a specific process for the sake of the other of the devices 310, 320 or the user thereof (e.g., an electronic gate (not shown) interworking with the second device 320 is opened for the sake of the user of the first device 310.) In the above example, identification information (e.g., a device serial number, a PIN number, a telephone number, etc.) of the first device 310, which may be previously registered in the second device 320, may be further consulted.

Figure 5:
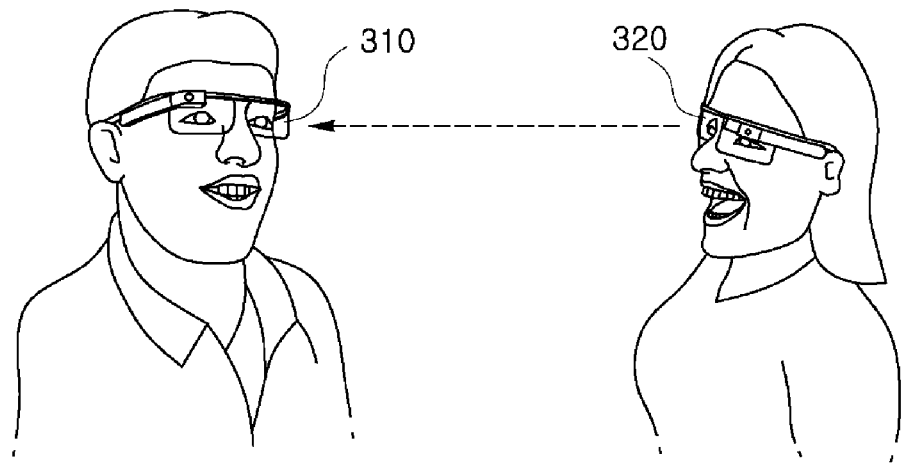
FIG. 5 is a reference view showing a case in which matching is made on the basis of nictitation of a user according to one embodiment of the invention.

FIG. 5 is a reference view showing a case in which matching is made on the basis of nictitation of a user according to one embodiment of the invention. As shown, both of the first device 310 and the second device 320 may be smart glasses. Here, the first device 310 may photograph nictitation of a user wearing the first device 310 by means of an inside camera (not shown). Next, the first device 310 may determine a pattern of the nictitation of the user on the basis of a plurality of photographed images. The above nictitation may also be photographed by means of an outside camera of the second device 320 (of the other user) observing it. The second device 320 may also independently determine a pattern of the nictitation on the basis of a plurality of photographed images. The two devices 310, 320 may be matched with each other on the basis of the separately determined patterns of the nictitation of the same user for the same time period.

Meanwhile, it will be appreciated by those skilled in the art that the above embodiment may also employ eye movement or pupil shape variation instead of nictitation.

Figure 6:
FIG. 6 is a reference view showing a case in which matching is made on the basis of pulsation of a user according to one embodiment of the invention.

FIG. 6 is a reference view showing a case in which matching is made on the basis of pulsation of a user according to one embodiment of the invention. As shown, the first device 310 may be a smart phone and the second device 320 may be a display device. Here, the first device 310 may measure pulsation of a user holding the first device 310 by means of a pulsation sensor (not shown). Next, the first device 310 may determine a pattern of a pulsation signal. In connection with the pulsation signal, the second device 320 may observe variation in complexion of the user (i.e., variation in glow or the like according to the pulsation) by means of a camera thereof (not shown). On the basis thereof, the second device 320 may independently determine a pattern of the pulsation signal. The two devices 310, 320 may be matched with each other on the basis of the separately determined patterns of the pulsation signal of the same user for the same time period.

(2) The case in which the second device 320 directly receives an input associated with a gesture of a user of the first device 310

It is assumed that the first device 310 may identify a biological state generated according to a gesture of a body part (e.g., right wrist) of a user thereof (e.g., an electromyogram state of the wrist of the user or a brainwave state of the user), like a smart watch or a smart band, and that the second device 320 includes or at least communicates with a touch panel for receiving a touch input associated with the above gesture of the user of the first device 310, a pointing tool (e.g., a mouse, a stylus, an electronic pen, etc.) for sensing a motion associated with the above gesture of the user of the first device 310, or other input tools (e.g. buttons, a keyboard, etc.)

According to the gesture of the user of the first device 310, the characteristic information on the biological state of the user may be determined as described above. Further, the application of the second device 320 may determine characteristic information on a touch input associated with the gesture, a motion input of a pointing tool, or a press input of other input tools (i.e., the characteristic information from the perspective of the second device 320). The determined information may also be provided to the matching system 200, or may be provided to the first device 310, if necessary.

The matching system 200, the first device 310, or the second device 320 may match the first device 310 and the second device 320 on the basis of the characteristic information on the biological state of the user of the first device 310 according to the gesture of the user, and the characteristic information on the input to the second device 320 according to the gesture of the user, and may accordingly notify the matching to at least one of the first device 310 and the second device 320.

At least one of the first device 310 and the second device 320 may perform various processes on the basis of the matching. For example, if the user of the first device 310 makes a series of sequential touches on a touch panel of the second device 320 (e.g., touches to quickly or slowly tap the touch panel several times), with the first device 310 worn on the right wrist (if right-handed), then the second device 320 may employ the above series of sequential touches and identification information (e.g., a device serial number, a PIN number, a telephone number, etc.) of the first device 310, which may be previously registered in the second device 320, as a key to perform authentication for permitting the user of the first device 310 to use the second device 320 only when none other than the user shows an intention to use the second device 320 by making the series of sequential touches with the first device 310 worn on the right wrist.

(3) The case in which an operation associated with a gesture of a user of the first device 310 is performed on the second device 320

According to one embodiment of the invention, it is assumed that the first device 310 may identify a biological state generated according to a gesture of a body part (e.g., right wrist) of a user thereof (e.g., an electromyogram state of the wrist of the user or a brainwave state of the user), like a smart watch or a smart band, and that an operation on a graphical object (e.g., an unlock bar that can be slid to unlock, an icon of a specific file or application program, etc.) associated with the above gesture of the user of the first device 310 is performed on the second device 320.

According to the gesture of the user of the first device 310, the characteristic information on the biological state of the user may be determined as described above. Further, the application of the second device 320 may determine characteristic information on the operation on the graphical object associated with the gesture (i.e., the characteristic information from the perspective of the second device 320). The determined information may also be provided to the matching system 200, or may be provided to the first device 310, if necessary.

The matching system 200, the first device 310, or the second device 320 may match the first device 310 and the second device 320 on the basis of the characteristic information on the biological state of the user of the first device 310 according to the gesture of the user, and the characteristic information on the operation on the second device 320 according to the gesture of the user, and may accordingly notify the matching to at least one of the first device 310 and the second device 320.

At least one of the first device 310 and the second device 320 may perform various processes on the basis of the matching. For example, if the user of the first device 310 performs an operation of sliding an unlock bar of the second device 320, with the first device 310 worn on the right wrist (if right-handed), then the second device 320 may employ the gesture of the above operation and identification information (e.g., a device serial number, a PIN number, a telephone number, etc.) of the first device 310, which may be previously registered in the second device 320, as a key to perform authentication for permitting the user of the first device 310 to unlock the second device 320 only when the user performs a correct operation with the first device 310 worn on the right wrist.

Further, at least one of the first device 310 and the second device 320 may also perform another process on the basis of the matching. For example, if the user of the first device 310 performs an operation of (quickly) dragging an icon of a specific file of the second device 320 on a screen thereof, with the first device 310 worn on the right wrist (if right-handed), then the second device 320 may employ the gesture of the above operation and identification information (e.g., a device serial number, a PIN number, a telephone number, etc.) of the first device 310, which may be previously registered in the second device 320, as a key to allow the file to be transferred from the second device 320 and stored in an account of a cloud server (not shown), which may be previously registered for the user of the first device 310, only when the user performs a proper operation with the first device 310 worn on the right wrist. In this case, the file may be first stored in the matching system 200 and then stored in the cloud server.

According to another embodiment of the invention, it is assumed that the first device 310 may identify a gesture of a body part (e.g., right wrist) of a user thereof, like a smart watch or a smart band, and that an action or operation associated with the above gesture of the user of the first device 310 is performed for a specific application program (e.g., a web browser or a mobile game) running on the second device 320.

The characteristic information on the biological state of the user of the first device 310, which is associated with the gesture of the user, may be determined as described above. Further, the application running on the second device 320 may determine characteristic information on the action or operation therefor associated with the gesture. For example, if the gesture of the user of the first device 310 is a touch action for (a graphical object of) the application running on the second device 320 (preferably, an action including sweep, an action including several taps, or other action having some pattern), the application may sense the touch action and then determine the characteristic information thereon. The determined information may also be provided to the matching system 200, or may be provided to the first device 310, if necessary.

The matching system 200, the first device 310, or the second device 320 may match the first device 310 and the second device 320 on the basis of the characteristic information on the biological state of the user of the first device 310 and the characteristic information on the action or operation of the user for the application running on the second device 320, and may accordingly notify the matching to at least one of the first device 310 and the second device 320.

At least one of the first device 310 and the second device 320 may perform various processes on the basis of the matching. For example, if the user of the first device 310 performs a touch action for a web browser (displaying a portal site for which the user has signed up) running on the second device 320, with the first device 310 worn on the wrist, then the second device 320 may employ the gesture of the above touch action and login information for the portal site of the user of the first device 310, which may be previously registered in the first device 310, as a key to allow the user to login to the portal site without requiring additional actions.

Figure 7:
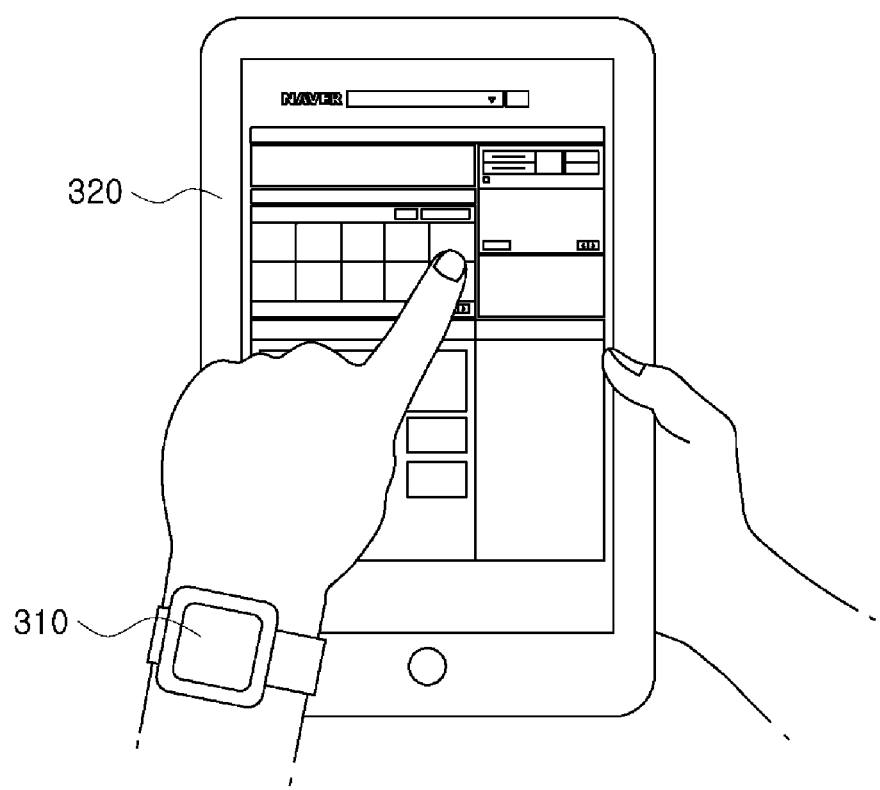
FIG. 7 is a reference view showing a situation in which a user of a first device performs a touch action for a web browser running on a second device so as to conveniently login to a portal site displayed in the web browser, according to one embodiment of the invention.

In connection with the above embodiment, reference may be made to FIG. 7, which is a view showing a situation in which the user of the first device 310 performs a touch action for the web browser running on the second device 320 so as to conveniently login to the portal site displayed in the web browser.

Although the characteristic information from the perspective of the second device 320 has been illustrated as various information on an input or operation according to a gesture of a user in the embodiments of (2) and (3), it may also preferably be regarding a pattern in which an input or operation is performed within a predetermined time window.

(4) The case in which the second device 320 directly measures brainwave, respiration, pulsation, electrocardiogram, electromyogram, or the like of a user of the first device 310

It is assumed that the first device 310 may determine characteristic information on a biological state of a user thereof, and that the second device 320 may independently determine characteristic information on the same type of biological state of the user.

Figure 8:
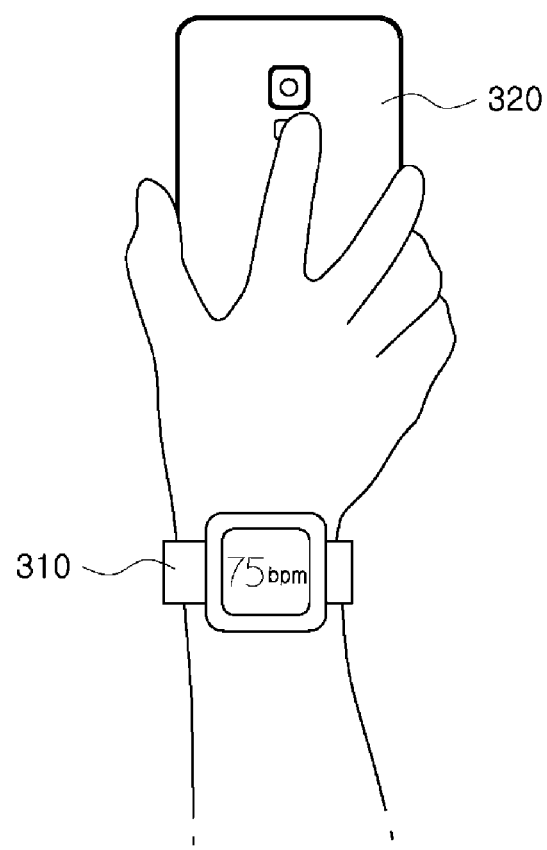
FIG. 8 is a reference view showing a case in which a first device and a second device are matched with each other according to one embodiment of the invention.

For example, the above assumption may be such that the first device 310 is a smart watch in a worn-on condition which may passively measure pulsation in a wrist of the user by means of an application thereof, and the second device 320 is a smart phone which may independently measure pulsation of the user by means of an application thereof when the user actively puts a finger on a pulsation sensor included in the second device 320. The information determined by the second device 320 may be provided to the matching system 200, or may be provided to the first device 310, as necessary. FIG. 8 is a view showing a case in which the first device 310 and the second device 320 are matched with each other according to the above embodiment.

For another example, the above assumption may be such that the first device 310 is a smart watch in a worn-on condition which may measure an electromyogram in a wrist of the user by means of an application thereof, and the second device 320 is a smart band in a worn-on condition which may measure an electromyogram in a forearm of the same user by means of an application thereof. Likewise, the information determined by the second device 320 may be provided to the matching system 200, or may be provided to the first device 310, as necessary.

The matching system 200, the first device 310, or the second device 320 may match the first device 310 and the second device 320 on the basis of the pieces of the characteristic information on the biological state of the user of the first device 310, and may accordingly notify the matching to at least one of the first device 310 and the second device 320.

At least one of the first device 310 and the second device 320 may perform various processes on the basis of the matching. For example, it is enabled that information (e.g. a computer file) is transmitted or received between the devices 310, 320, or that one of the devices 310, 320 or the user thereof performs a specific process for the sake of the other of the devices 310, 320 or the user thereof (e.g., an elevator (not shown) interworking with the second device 320 is requested for the sake of the user of the first device 310, and then the elevator is automatically requested to ascend or descend to a floor frequently visited by the user of the first device 310.)

Meanwhile, although it has been mainly described herein that various types of characteristic information on the devices 310, 320 may be a wave representing a pattern regarding a biological state of a specific user, or property information thereof, the basis information may also be adopted with reference to prior art without limitation, as long as it is regarding the biological state of the user. Meanwhile, examples of the types of the property information of the wave include the following:

Types of the property information of the wave in time domain: maximum amplitude, average amplitude, average frequency, mean, standard deviation, standard deviation normalized by overall amplitude, variance, skewness, kurtosis, sum, absolute sum, root mean square (RMS), crest factor, dispersion, entropy, power sum, center of mass, coefficients of variation, cross correlation, zero-crossings, seasonality, DC bias, or the above properties computed for a first, second, third or higher order derivative of the wave; and Types of the property information of the wave in frequency domain: spectral centroid, spectral density, spherical harmonics, total average spectral energy, band energy ratios for every octave, log spectral band ratios, linear prediction-based cepstral coefficients (LP-CCs), perceptual linear prediction (PLP) cepstral coefficients, mel-frequency cepstral coefficients, frequency topology, or the above properties computed for a first, second, third or higher order derivative of a frequency domain representation of the wave.

Meanwhile, although it has been illustratively described herein that the application of the first device 310 or the application of the second device 320 determines various types of characteristic information according to the biological state of the user of the first device 310, it is apparent that at least a part of the determination of the characteristic information may also be performed by the matching system 200, which may perform the matching according to the invention.

Meanwhile, although it has been described herein that the matching is made on the basis of the characteristic information on a biological state of a user determined from a perspective of the first device and the characteristic information associated with or generated according to the biological state of the user determined from a perspective of the second device, information based on conventional biological information identification techniques or other authentication techniques may be further consulted to assist the matching. For example, when the matching is made between the two devices 310, 320 on the basis of nictitation of a specific user, the matching may be confirmed on the further basis of a fact that a pupil image of the user, which has been previously stored in the matching system 200, is at least partially detected by the two devices 310, 320.

Second embodiment

A variety of matching methods have been described in connection with the first embodiment. The matching is basically made when an association, which is diverse as described above, is recognized between the first device 310 and the second device 320. The required degree of association may be adaptively changed as necessary.

That is, the matching system 200, the first device 310, or the second device 320 may adjust (alleviate) the degree of association required for the matching, with respect to the characteristic information on a biological state of a user determined by the first device 310 and the characteristic information associated with or generated according to the biological state of the user determined by the second device 320. The alleviation may be performed on the basis of (i) a history indicating that the first device 310 and the second device 320 have been matched before, (ii) a proof that the first device 310 and the second device 320 have been used or are owned by the same user (e.g., travel route information, owner information or the like of the devices), or (iii) a fact that the first device 310 and the second device 320 use the same communication network 100 (e.g., the same Wi-Fi access point (AP)).

Specifically, the alleviation may preferably be implemented in a manner of recognizing an association, for example, even if the two devices 310, 320 exhibit the association for fewer times or for a shorter time period, or even if a signature or pattern is partially inputted.

The Case in which Three or More Devices are Matched

As described above, the matching according to the invention is basically made between one first device 310 and one second device 320. However, the present invention may also be very useful when multiple devices act as different first devices 310 in relation to the second device 320, respectively.

Figure 9:
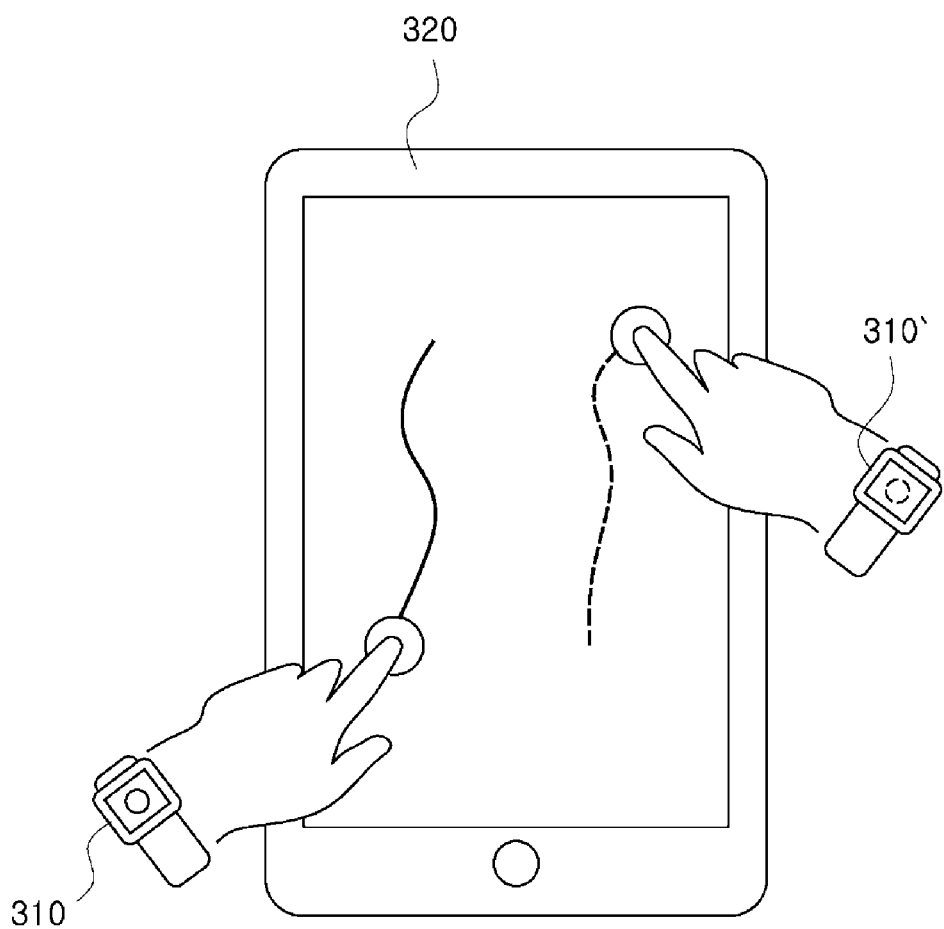
FIG. 9 is a reference view showing that two first devices are respectively matched with one second device according to one embodiment of the invention.

FIG. 9 is a view showing that two first devices 310, 310' are respectively matched with one second device 320 according to one embodiment of the invention. That is, when it is determined that multiple first devices 310, 310' are matched with the second device 320, the second device 320 may provide different types of user experience with respect to the input of each of the matched counterparts. The different types of user experience may be different forms of touch trace lines as shown, but may also be different sound responses or tactual responses.

Meanwhile, when the first device 310 and the second device 320 are matched and paired with each other, there may be another third device that is matched only with one of them. In this case, the other of the pair of the devices 310, 320 may be automatically matched with the third device. The above-described association may not be necessarily required for the automatic matching.

Main Steps of the Matching Methods

Figure 2:
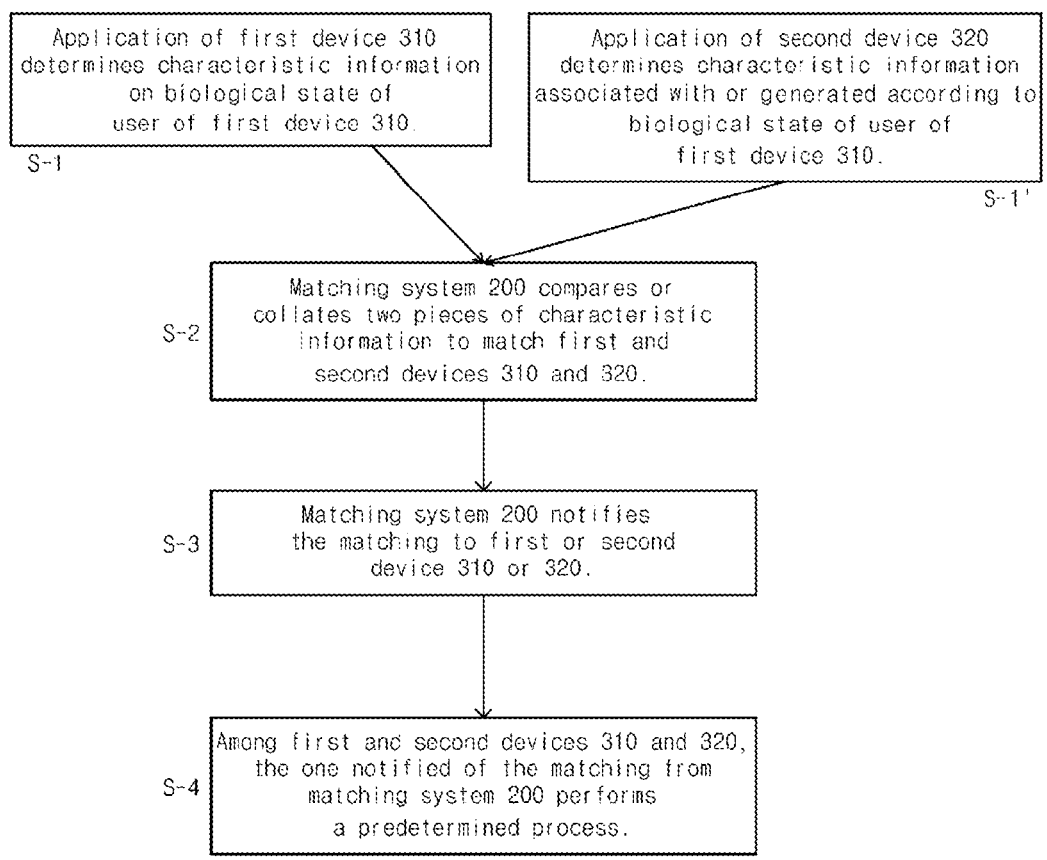
FIG. 2 is a flow chart showing the main steps of a matching method according to one embodiment of the invention.

As described above, the matching methods of the invention may be implemented with various embodiments. Referring to FIG. 2, the main steps of the matching methods, which may be common to those embodiments, will be discussed. FIG. 2 is a flow chart showing the main steps of a matching method according to one embodiment of the invention.

In step S-1, an application of the first device 310 may determine characteristic information on a biological state of a user of the first device 310.

Further, in step S-1', an application of the second device 320 may determine characteristic information associated with or generated according to the biological state of the user of the first device 310.

Here, any one of step S-1 and step S-1' may precede the other, or both may be performed at the same time.

Next, in step S-2, the matching system 200 may compare or collate the two pieces of the characteristic information to match the first device 310 and the second device 320.

Next, in step S-3, the matching system 200 may notify the matching to the first device 310 or the second device 320.

Lastly, in step S-4, among the first device 310 and the second device 320, the one notified of the matching from the matching system 200 may perform a predetermined process.

The embodiments according to the invention as described above may be implemented in the form of program instructions that can be executed by various computer components, and may be stored on a computer-readable recording medium. The computer-readable recording medium may include program instructions, data files, data structures and the like, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be changed to one or more software modules to perform the processes of the present invention, and vice versa.

Although the present invention has been described in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A matching method comprising the steps of:
   receiving, by a matching system, first characteristic information on a biological state of a user from a first device, wherein the first characteristic information is determined by the first device based on a pattern of values related to the biological state of the user, and the values are obtained by a sensing element of the first device;
   receiving, by the matching system, second characteristic information associated with or generated according to the biological state of the user from a second device, wherein the second characteristic information determined by the second device based on data related to the biological state of the user, and the data is obtained by a sensing element of the second device; and
   matching, by the matching system, the first device with the second device on the basis of the first characteristic information and the second characteristic information, wherein matching the first device with the second device comprises at least one of indicating that the first device and the second device belong to the user, indicating that the first device and the second device function for the sake of the user, indicating that the first device and the second device are located substantially close to each other, or indicating that one of the first device and the second device is competent to authenticate or permit the other of the first device and the second device.

2. The method of claim 1, wherein the sensing element of first device includes at least one of a brainwave sensor, a respiration sensor, a pulsation sensor, an electrocardiogram sensor, an electromyogram sensor, and a camera, and
   the first characteristic information is internally determined in the first device.

3. The method of claim 1, wherein the second characteristic information is information on a pattern of the data obtained by the sensing element of the second device by photographing or optically sensing the biological state of the user.

4. The method of claim 1, wherein the second characteristic information is information on an input to the second device according to a gesture of the user.

5. The method of claim 1, wherein the second characteristic information is information on an operation on the second device according to a gesture of the user.

6. The method of claim 1, wherein the second characteristic information is information on the biological state of the user.

7. The method of claim 1, wherein the matching is temporary.

8. The method of claim 1, wherein the matching the first device with the second device comprises generating a notice indicating the matching by the first device or the second device.

9. The method of claim 1, wherein the matching step comprises consulting biological information identified with respect to the user.

10. A device comprising:
    a sensing element;
    a memory;
    a processor; and
    program circuitry including computer readable instructions which, when executed by the processor, cause the program circuitry to determine, on the basis of a value regarding biological information of a user of the device, first characteristic information on a biological state of the user,
    wherein the value is obtained by the sensing element, and the device is matched with an external device on the basis of the first characteristic information and second characteristic information, which is independently determined by the external device based on data related to the biological state of the user, associated with or generated according to the biological state of the user,
    wherein matching the device with the external device comprises at least one of indicating that the device and the external device belong to the user, indicating that the device and the external device function for the sake of the user, indicating that the device and the external device are located substantially close to each other, or indicating that one of the device and the external device is competent to authenticate or permit the other of the device and the external device.

11. The device of claim 10, wherein the sensing element comprises at least one of a brainwave sensor, a respiration sensor, a pulsation sensor, an electrocardiogram sensor, an electromyogram sensor, and a camera, and
    wherein the value regarding the biological information of the user is calculated by means of at least one of the brainwave sensor, the respiration sensor, the pulsation sensor, the electrocardiogram sensor, the electromyogram sensor, and the camera.

12. A server system for matching, comprising:
a processor;
a communication unit configured to communicate with a first device and a second device;
a matching unit including computer readable instructions which, when executed by the processor, cause the matching unit to match the first device with the second device on the basis of first characteristic information on a biological state of a user from the first device and second characteristic information associated with or generated according to the biological state of the user from the second device; and
a storage for storing information provided from at least one of the first device and the second device,
wherein the first characteristic information is determined by the first device based on a pattern of values related to the biological state of the user, and the values are obtained by a sensing element of the first device, and
wherein the second characteristic information determined by the second device based on data related to the biological state of the user, and the data is obtained by a sensing element of the second device,
wherein matching the first device with the second device comprises at least one of indicating that the first device and the second device belong to the user, indicating that the first device and the second device function for the sake of the user, indicating that the first device and the second device are located substantially close to each other, or indicating that one of the first device and the second device is competent to authenticate or permit the other of the first device and the second device.

13. The server system of claim 12, wherein the sensing element of the first device includes at least one of a brainwave sensor, a respiration sensor, a pulsation sensor, an electrocardiogram sensor, an electromyogram sensor, and a camera, and
the first characteristic information is internally determined in the first device.

14. The server system of claim 12, wherein the second characteristic information is information on a pattern of the data obtained by the sensing element of the second device by photographing or optically sensing the biological state of the user.

15. The server system of claim 12, wherein the second characteristic information is information on an input to the second device according to a gesture of the user.

16. The server system of claim 12, wherein the second characteristic information is information on an operation on the second device according to a gesture of the user.

17. The server system of claim 12, wherein the second characteristic information is information on the biological state of the user.

* * * * *